US00PP08847P

United States Patent [19]

Meilland

[11] Patent Number: Plant 8,847

[45] Date of Patent: Jul. 26, 1994

[54] ROSE PLANT — MEIMOUSLIN VARIETY

[75] Inventor: Alain A. Meilland, Antibes, France

[73] Assignee: The Conard-Pyle Company, West Grove, Pa.

[21] Appl. No.: 86,865

[22] Filed: Jul. 7, 1993

[51] Int. Cl.[5] ..... A01H 5/00

[52] U.S. Cl. ..... Plt./21

[58] Field of Search ..... Plt. 20, 21, 28, 29

*Primary Examiner*—Howard J. Locker

*Attorney, Agent, or Firm*—Burns, Doane, Swecker & Mathis

[57] ABSTRACT

A new and distinct variety of Grandiflora rose plant is provided which abundantly and continuously forms attractive fully double large long-lasting blossoms of relatively stable coloration that are Strawberry Red on the upper side and Cardinal Red on the under side. The blossom petals frequently are indented and the blossoms exhibit a slight fragrance. The plant exhibits a bushy growth habit, tends to be regular and somewhat low-growing, forms medium green adult wood, forms strong and vigorous vegetation, and is well suited for service as attractive ornamentation in parks and gardens. Additionally, the plant is not particularly affected by cryptogamic diseases.

1 Drawing Sheet

SUMMARY OF THE INVENTION

The new variety of Grandiflora rose plant was created by artificial pollination wherein two parents were crossed which previously had been studied in the hope that they would contribute the desired characteristics. The female parent (i.e., the seed parent) of the new variety was the Olympiad variety (nonpatented in the United States). The male parent (i.e., the pollen parent) was the product of the cross of the Meifersi variety (nonpatented in the United States) and the Red Lady variety (nonpatented in the United States). The parentage of the new variety can be summarized as follows:

Olympiad × (Meifersi × Red Lady).

The seeds resulting from the above pollination were sown and 45 small plants were obtained which were physically and biologically different from each other. Selective study resulted in the identification of a single plant of the new variety.

It was found that the new variety of Grandiflora rose plant of the present invention possesses the following combination of characteristics:

(a) forms in abundance on a continuous basis attractive large long-lasting fully double blossoms of relatively stable coloration which are Strawberry Red on the upper side and Cardinal Red on the under side,
(b) forms blossoms which exhibit a slight fragrance,
(c) forms blossom petals that commonly are indented,
(d) forms medium green adult wood,
(e) exhibits strong and vigorous vegetation,
(f) exhibits a bushy and somewhat regular growth habit,
(g) is particularly suited for growing in parks and gardens, and
(h) is not particularly affected by cryptogamic diseases.

The new variety well meets the needs of the horitcultural industry and is particularly well suited for use as attractive ornamentation in the landscape.

The new variety has been found to undergo asexual propagation by a number of routes, including budding, grafting, cuttage, etc. Asexual propagation by the above-mentioned methods as performed in France has shown that the characteristics of the new variety are strictly transmissible from one generation to another.

The new variety has been named the Meimouslin variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were two years of age and were observed during October while budded on *Rosa froebelli* understock and growing outdoors at LeCannet-des-Maures, Var, France.

DETAILED DESCRIPTION

Figures 1, 2, 3, 4, 5, 6, 7, 8, 9, 10, 11, 12, 13, 14, 15, 16:
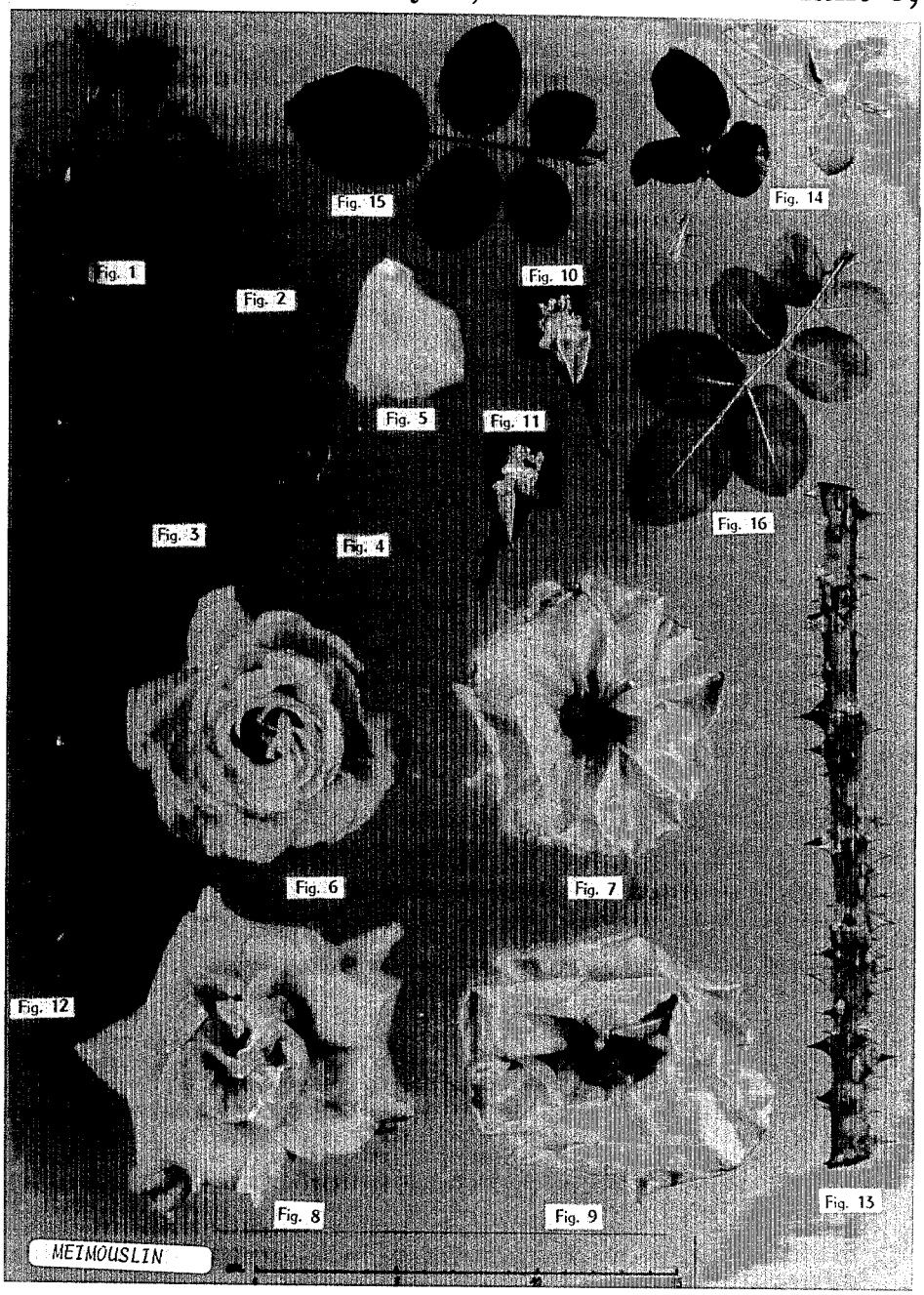
FIG. 1 illustrates a specimen of a young shoot.
FIG. 2 illustrates a specimen of a floral bud before the opening of the sepals.
FIG. 3 illustrates a specimen of a floral bud at the opening of the sepals.
FIG. 4 illustrates a specimen of a floral bud at the opening of the petals.
FIG. 5 illustrates a specimen of a flower petal.
FIG. 6 illustrates a specimen of an open flower—plan view—obverse.
FIG. 7 illustrates a specimen of an open flower—plan view—reverse.
FIG. 8 illustrates a specimen of a fully open flower—plan view—obverse.
FIG. 9 illustrates a specimen of a fully open flower—plan view—reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates a specimen of a pair of leaves having three leaflets—plan view—upper surface (left) and lower surface (right)
FIG. 15 illustrates a specimen of a leaf with five leaflets—plan view—upper surface.
FIG. 16 illustrates a specimen of a leaf with seven leaflets—plan view—under surface.

The chart used in the identification of the colors is that of the Royal Horticultural Society (R.H.S. Colour Chart). The description is based on the observation of two year-old plants made during October while budded on *Rosa froebelli* understock and growing outdoors at LeCannet-des-Maures, Var, France. The coloration in common terms precedes reference to the chart.

Class: Grandiflora.

Plant:

*Height.*—Approximately 80 to 100 cm. on average.

*Habit.*—Bushy, semi-erect.

Branches:

*Color.*—Young stems: Lettuce Green, Yellow-Green Group 144B, widely suffused with reddish coloration. Adult wood: Medium green, Yellow-Green Group 146B.

*Thorns.*—Size: fairly large. Quantity: numerous with many prickles. Color: reddish on young stems and pinkish on mature wood.

Leaves:

*Stipules.*—Adnate, pectinate, narrow and linear.

*Petioles.*—Upper surface: striped reddish brown on young foliage and medium green on adult foliage with more or less glandular edges. Under surface: light green, and bears a few prickles.

*Leaflets.*—Number: 3, 5 (most often), and 7. Shape: oval. Serration: single and regular. Texture: consistent. General appearance: dense, dark and glossy foliage. Color (young foliage): Upper surface: Bronze Green, Yellow-Green Group 146A, more or less stained with reddish coloration. Under surface: light green, Yellow-Green Group 146C, more or less stained with reddish coloration. Color (adult foliage): Upper surface: dark green, Yellow-Green Group 147A. Under surface: medium green, Green Group 138A.

Inflorescence:

*Number of flowers.*—Usually one to three blooms per stem.

*Peduncle.*—Light green, and widely stained with reddish coloration. The length is approximately 5 to 5.5 cm. on average.

*Sepals.*—Upper surface: tomentose, greenish and more or less stained with reddish coloration. Under surface: light green and more or less stained with reddish coloration.

*Buds.*—Shape: ovoid. Length: approximately 2.5 cm. on average. Size: medium. Color upon opening: Upper surface: dark velvety Currant Red, Red Group 46A. Under surface: Cardinal Red, Red Group 53A.

*Flower.*—Shape: cuplike and fully double. Diameter: approximately 10 to 11 cm. on average. Color (when opening begins): Upper surface: Strawberry Red, Red Group 46B, very bright and velvety. Under surface: Cardinal Red, Red Group 53B, darker near the base. Color (when blooming): Upper surface: Strawberry Red, Red Group 46B, bright and velvety. Under surface: Cardinal Red, Red Group 53B, darker near the base. Color (at end of opening): Upper surface: Strawberry Red, Red Group 46B, bright and velvety. Under surface: Cardinal Red, Red Group 53B, darker near the base. Fragrance: slight. Lasting quality: very long-lasting bloom when on the plant or when cut and placed in a vase. Petal number: approximately 27 to 35 on average. Petal shape: rounded to flat with edges that often are indented. Texture: very consistent. Petal drop: good. Stamen number: approximately 132 on average. Anthers: straw ochre. Filaments: orange yellow in coloration and of irregular heights. Pistils: approximately 161 on average. Stigmas: normal, straw colored. Styles: straw colored with fuschia tips, tomentose near the base, and of irregular heights. Receptacle: medium green, more or less stained with reddish coloration, in longitudinal section at the dehiscence of the anthers it is in the shape of a wide pitcher.

Development:

*Vegetation.*—Strong and vigorous.

*Blooming.*—Abundant and continuous.

*Aptitude to bear fruits.*—Good.

*Resistance to frost.*—Good.

*Resistance to diseases.*—Good.

I claim:

1. A new and distinct variety of Grandiflora rose plant characterized by the following combination of characteristics:

(a) forms in abundance on a continuous basis attractive large long-lasting fully double blossoms of relatively stable coloration which are Strawberry Red on the upper side and Cardinal Red on the under side,
(b) forms blossoms which exhibit a slight fragrance,
(c) forms blossom petals that commonly are indented.
(d) forms medium green adult wood,
(e) exhibits strong and vigorous vegetation,
(f) exhibits a bushy and somewhat regular growth habit,
(g) is particularly suited for growing in parks and gardens, and
(h) is not particularly affected by cryptogamic diseases;

substantially as herein shown and described.

* * * * *

MEIMOUSLIN